(12) United States Patent  (10) Patent No.: US 10,517,715 B2
Cournoyer et al.                    (45) Date of Patent:    Dec. 31, 2019

(54) REINFORCEMENT INSERT FOR TISSUE GRAFT

(71) Applicant: Medos International Sàrl, Le Locle (CH)

(72) Inventors: John R. Cournoyer, Raynham, MA (US); Karthik Lavakumar, Framingham, MA (US)

(73) Assignee: Medos International Sarl, Le Locle (CH)

( * ) Notice: Subject to any disclaimer, the term of this patent is extended or adjusted under 35 U.S.C. 154(b) by 452 days.

(21) Appl. No.: 14/494,346

(22) Filed: Sep. 23, 2014

(65) Prior Publication Data

US 2016/0081790 A1    Mar. 24, 2016

(51) Int. Cl.
*A61F 2/08*    (2006.01)

(52) U.S. Cl.
CPC ....... *A61F 2/0811* (2013.01); *A61F 2002/087* (2013.01); *A61F 2002/0829* (2013.01); *A61F 2002/0852* (2013.01); *A61F 2230/0069* (2013.01)

(58) Field of Classification Search
CPC ............ A61F 2/0811; A61F 2230/0069; A61F 2002/0829; A61F 2002/087; A61F 2002/0852
See application file for complete search history.

(56) References Cited

U.S. PATENT DOCUMENTS

| | | | |
|---|---|---|---|
| 4,950,270 A | 8/1990 | Bowman et al. | |
| 5,849,013 A | 12/1998 | Whittaker et al. | |
| 5,860,978 A | 1/1999 | McDevitt et al. | |
| 5,968,045 A * | 10/1999 | Frazier | A61B 17/864 606/232 |
| 6,001,100 A | 12/1999 | Sherman et al. | |
| 6,010,503 A * | 1/2000 | Richelsoph | A61B 17/7032 606/278 |
| 6,059,818 A | 5/2000 | Johnson et al. | |
| 6,302,886 B1 | 10/2001 | McDevitt et al. | |
| 6,730,124 B2 | 5/2004 | Steiner | |
| 6,890,354 B2 | 5/2005 | Steiner et al. | |
| 7,137,996 B2 | 11/2006 | Steiner et al. | |

(Continued)

OTHER PUBLICATIONS

[No Author Given] "ACL Graft Choices," Centers for Orthopedics, http://www.orthoassociates.com/SP11B35, accessed Aug. 11, 2015 (8 pages).

(Continued)

*Primary Examiner* — Brian A Dukert

(57) ABSTRACT

Devices and methods for reinforcing tissue grafts are described herein. In one embodiment, an implant is described that includes a proximal end portion having a through-hole formed therein, a distal end portion, and a reinforcing insert disposed in the through-hole. The insert includes a proximal face, a distal face opposed to the proximal face, a first upper surface extending between the proximal and distal faces and having a generally convex shape that abuts against at least a portion of a sidewall of the through-hole, and a second lower surface extending between the proximal and distal faces and having a generally concave shape. The second lower surface and portions of the sidewall of the through-hole not abutted by the first upper surface form a reinforced through-hole of the implant.

18 Claims, 8 Drawing Sheets

(56) References Cited

U.S. PATENT DOCUMENTS

| | | | |
|---|---|---|---|
| 7,141,066 B2 | 11/2006 | Steiner et al. | |
| 7,201,773 B2 | 4/2007 | Steiner et al. | |
| 7,235,074 B1* | 6/2007 | Sklar | A61F 2/0811 606/53 |
| 8,062,295 B2 | 11/2011 | McDevitt et al. | |
| 8,110,001 B2 | 2/2012 | Carter et al. | |
| 2003/0078585 A1 | 4/2003 | Johnson et al. | |
| 2003/0216780 A1* | 11/2003 | Fitts | A61F 2/0811 606/232 |
| 2004/0002735 A1* | 1/2004 | Lizardi | A61B 17/0401 606/232 |
| 2005/0159812 A1 | 7/2005 | Dinger et al. | |
| 2005/0203621 A1 | 9/2005 | Steiner et al. | |
| 2006/0089646 A1 | 4/2006 | Bonutti | |
| 2008/0086138 A1* | 4/2008 | Stone | A61B 17/0401 606/265 |
| 2008/0228271 A1* | 9/2008 | Stone | A61F 2/08 623/13.12 |
| 2010/0003640 A1 | 1/2010 | Damstra et al. | |
| 2010/0082104 A1* | 4/2010 | Carter | A61F 2/0811 623/13.14 |
| 2010/0274355 A1 | 10/2010 | McGuire et al. | |
| 2010/0324676 A1* | 12/2010 | Albertorio | A61B 17/0401 623/13.14 |
| 2011/0066185 A1 | 3/2011 | Wotton, III | |
| 2013/0116730 A1* | 5/2013 | Denham | A61B 17/0401 606/232 |
| 2014/0257346 A1 | 9/2014 | Sengun et al. | |
| 2015/0039026 A1 | 2/2015 | Pasquali et al. | |
| 2015/0157449 A1* | 6/2015 | Gustafson | A61F 2/0811 606/145 |

OTHER PUBLICATIONS

Edgar, C. M., et al., "Prospective Comparison of Auto and Allograft Hamstring Tendon Constructs for ACL Reconstruction," Clin. Orthop. Relat. Res., 2008, 2238-2246. (9 pages).

Marks, P. H., "Rigidfix™ ACL Cross Pin System," 1999, Surgical Technique guide (4 pages).

* cited by examiner

REINFORCEMENT INSERT FOR TISSUE GRAFT

FIELD

This application relates generally to surgical procedures and, more particularly, to soft tissue reconstruction surgery.

BACKGROUND

A surgeon often has a variety of graft choices for replacing soft tissue in surgical reconstruction procedures. Two possible options include autografts, tissues donated from the patient's own body, and allografts, tissue harvested from a donor, often a cadaver. Autografts can be beneficial because the graft is harvested directly from the host and is aged correctly for the host. However, the added procedure required to harvest the graft from the patient can result in additional pain and an extended post surgical recovery period. In contrast, allografts can provide added benefit over autografts because they do not require the patient to recover from a bone and/or soft tissue harvesting operation. This can result in a faster healing time and a reduced amount of physical therapy following the procedure.

Allografts, unlike organ transplants, do not usually pose a risk for rejection by the host and, after being harvested from a cadaver, they can be cleaned and frozen in liquid nitrogen for later use. Further, a cadaver can be screened for any illness which can be transferred to the host prior to harvesting any tissue or bone. However, the quality of an allograft is not always guaranteed. In the case of bone, for example, the quality of a graft can be dependent on the age and density of the bone being harvested. Additionally, chemical sterilization, irradiation, and other processing can compromise the quality of the bone.

Anterior Cruciate Ligament (ACL) repair is one example of a procedure where allografts are commonly utilized. Typically, a surgeon can replace a damaged ACL with a bone-tendon-bone (BTB) allograft taken from a cadaver's patellar tendon or other tissue. As shown in FIG. 1, the procedure generally requires preparing a patient's knee for ACL reconstruction by forming two bone tunnels 6, 8, one in the tibia and one in the femur. The BTB allograft 1 can be drawn first through the tibial tunnel 6 and the femoral tunnel 8 such that one bone plug can be secured within the tibia and the other can be secured within the femur. The surgeon can draw the BTB allograft 1 through the tibial and femoral tunnels by pulling on a suture that is threaded through the tunnels and a bore formed in the leading bone plug.

If the quality of the leading bone plug is poor, however, the suture can pull through the bone plug during implantation. This is because the narrow suture contacts the bone plug over a small area, and therefore imparts significant pressure onto the bone plug when a surgeon or other user pulls the graft through the tunnels 6, 8.

Accordingly, there is a need for improved devices and methods for reinforcing tissue grafts. More particularly, there is a need for improved bone plug reinforcement devices for use with tissue allografts.

SUMMARY

The devices and methods described herein generally provide improved implants that reinforce bone used in tissue grafts and can have a number of advantages, including the ability to reinforce a bone plug of any quality. Bone plug reinforcement inserts and implants including such inserts can redistribute a load applied by a suture while a graft is being implanted within a patient because the suture can be pulled against the insert and the insert can, in turn, be pulled against the upper surface of a bone plug through-hole. The redistribution of the load is made possible by the increased contact area between the bone plug insert and the bone plug through-hole, thereby reducing the pressure applied to the bone plug at any one point. The lower pressure can result in a lowered probability of bone plug failure. Additionally, in some embodiments the insert can be shaped such that it can be inserted into a bone plug through-hole in a manner that maintains a desired through-hole diameter and does not introduce new failure points by reducing the cross sectional area of the bone plug adjacent to the through-hole.

In one aspect, an implant can include a proximal end portion having a through-hole formed therein, a distal end portion, and a reinforcing insert disposed in the through-hole. The reinforcing insert can include a proximal face, a distal face opposed to the proximal face, and a first upper surface extending between the proximal and distal faces. The upper surface can have a generally convex shape that abuts against at least a portion of a sidewall of the through-hole. The insert can further include a second lower surface extending between the proximal and distal faces. The lower surface can be opposed to and disposed below the first upper surface, and can have a generally concave shape. The second lower surface and portions of the sidewall of the through-hole not abutted by the first upper surface can form a reinforced through-hole of the implant.

The devices and methods described herein can include any number of variations or additional features, all of which are considered to be within the scope of the present invention. For example, in some embodiments, a radius of curvature of the first upper surface of the reinforcing insert associated with the generally convex shape can be approximately equal to a radius of curvature of the portion of the sidewall of the through-hole against which the first upper surface abuts. In other embodiments, a radius of curvature of the second lower surface of the reinforcing insert associated with the generally concave shape can be approximately equal to a radius of the through-hole.

In some embodiments, a distance between a midpoint of the convex surface and a midpoint of the concave surface can be in a range between about 0.5 millimeters and about 3 millimeters. In one embodiment, the distance can be about 1 millimeter. In some embodiments, at least one of the proximal and distal faces can have a cavity formed therein for receiving an insertion tool. In some embodiments, the cavity can have a height and a width that are each in a range between about 0.5 mm and about 1.0 mm.

In certain embodiments, the implant can further include a suture disposed in the reinforced through-hole. The suture can be manipulated by a surgeon or other user to pull the implant into position within a bone tunnel, and the reinforcing insert can be positioned between the sidewall of the through-hole and the suture during such an operation.

In other embodiments, the implant can be a bone plug. Indeed, in some embodiments the bone plug can be a bone-tendon-bone graft. In such an embodiment, a first bone portion of the implant can be part of the proximal end portion of the implant, a second bone portion of the implant can be part of the distal end portion of the implant, and a tendon can extend between the first and second bone portions.

The reinforced through-hole in the proximal end portion of the implant can have a variety of shapes and sizes. In some embodiments, for example, a cross-section of the reinforced through-hole can have a circular shape. This can be true even if, in certain embodiments, the cross-section of the through-hole has a non-circular shape.

In another aspect, a reinforced bone plug can include a bone plug having a substantially cylindrical shape and a through-hole extending transversely across a longitudinal axis of the bone plug. The reinforced bone plug can also include an insert positioned within the through-hole such that a convex surface of the insert abuts against at least a portion of a sidewall of the through-hole and an opposing concave surface of the insert intersects at least a second portion of the sidewall of the through-hole to define a reinforced through-hole in the bone plug.

Similar to the implant described above, the reinforced bone plug can include any number of variations or additional features, all of which are considered to be within the scope of the present invention. In some embodiments, for example, a cross-section of the through-hole can be oblong and a cross-section of the reinforced through-hole can be substantially circular.

In still other embodiments, a radius of curvature of the convex surface can be substantially equal to a radius of curvature of the portion of the sidewall of the through-hole against which it abuts. In other embodiments, a radius of curvature of the concave surface can be substantially equal to a radius of curvature of the second portion of the sidewall of the through-hole.

In addition, in certain embodiments the reinforced bone plug can further include a suture disposed in the reinforced through-hole. As mentioned above, the suture can be manipulated by a surgeon or other user to pull the implant into position within a bone tunnel, and the insert can be positioned between the sidewall of the through-hole and the suture during such an operation.

In another aspect, a method for soft tissue surgical reconstruction can include forming a through-hole in a proximal end portion of an implant and positioning an insert having a convex surface opposed to a concave surface within the through-hole such that the convex surface abuts against at least a portion of a sidewall of the through-hole to form a reinforced through-hole. The method can also include threading a suture through the reinforced through-hole, and drawing the implant into a bone tunnel by pulling on the suture threaded through the reinforced through-hole.

In some embodiments, the through-hole can have an oblong shape. In other embodiments, the suture can abut against the concave surface of the insert when pulled to draw the implant into the bone tunnel. In still other embodiments, the implant can include a bone plug having a tendon coupled thereto, the through-hole can be formed in the bone plug, and the portion of the sidewall of the through-hole against which the convex surface abuts can be a proximal end portion of the sidewall disposed at a location that is opposite to the tendon coupled to the bone plug.

In another aspect, a method for reinforcing a bone plug can include positioning an insert having a convex surface opposed to a concave surface within a through-hole formed in a bone plug such that a convex surface of the insert abuts against at least a portion of a sidewall of the through-hole and the concave surface of the insert and other portions of the sidewall of the through-hole form a reinforced through-hole for the bone plug.

In some embodiments, the method can also include expanding the through-hole to form an oblong through-hole prior to positioning the insert within the through-hole formed in the bone plug. In certain embodiments, a width of the oblong through-hole can be approximately the same as a diameter of the through-hole prior to being expanded. In still other embodiments, the portion of the sidewall of the through-hole against which the convex surface abuts can be the most proximal portion of the sidewall, the portion of the sidewall being disposed at a location that is opposed to an end of the bone plug being configured to have a tendon associated therewith.

In another aspect, a bone plug reinforcing insert can include a proximal face, a distal face opposed to the proximal face, and a first upper surface extending between the proximal face and the distal face and having a generally convex shape. The insert can also include a second lower surface extending between the proximal face and the distal face, the second lower surface being opposed to and disposed below the first upper surface, and the second lower surface having a generally concave shape. Further, the insert can be configured to be positioned within a bone plug through-hole such that the first upper surface abuts against at least a portion of a sidewall of the through-hole.

The bone plug inserts described herein can be formed from a variety of biocompatible materials known in the art. The insert can be formed from materials having a strength or density greater than that of the bone plug itself, so as to ensure that a suture cannot pull through the insert. In some embodiments, for example, the bone plug can be made from a polymer, a metal, or another biocompatible material. Suitable biocompatible materials can include, for example, metals such as stainless steel and titanium. In certain embodiments, different components can be made from different materials, e.g., the insertion tools discussed below can be formed from a metal material, while the bone plug insert can be formed from a polymer.

As mentioned above, the bone plug reinforcing inserts described herein can be shaped and sized to fit within a variety of different bone plug through-holes. For example, the bone plug through-hole can have a symmetric (e.g., circular, elliptical, etc.) shape, or an asymmetric shape.

In another aspect, a bone plug can include a graft having a proximal end and a distal end, the proximal end having a through-hole formed therein, and the through-hole having a bone plug reinforcing insert as described above disposed therein such that the first upper surface of the insert abuts against at least a first portion of a sidewall of the through-hole and the second lower surface of the insert and a second portion of the through-hole form a reinforced through-hole.

In another aspect, a reinforced bone plug includes a bone plug having a substantially cylindrical shape and a through-hole extending transversely across a longitudinal axis of the bone plug. The reinforced bone plug also includes an insert positioned within the through-hole such that a convex surface of the insert abuts against at least a portion of a sidewall of the through-hole and an opposing concave surface intersects at least a second portion of the sidewall of the through-hole to define a reinforced through-hole in the bone plug.

In some embodiments, a cross-section of the through-hole can be oblong and a cross-section of the reinforced through-hole can be substantially circular. In other embodiments, a radius of curvature of the convex surface can be substantially equal to a radius of curvature of the portion of the sidewall of the through-hole against which it abuts. In still other embodiments, a radius of curvature of the concave surface can be substantially equal to a radius of curvature of the second portion of the sidewall of the through-hole. The radii of curvature discussed above can have any of a variety of values, but in some embodiments can be about 2 millimeters each.

BRIEF DESCRIPTION OF THE DRAWINGS

The aspects and embodiments of the invention described above will be more fully understood from the following detailed description taken in conjunction with the accompanying drawings, in which.

DETAILED DESCRIPTION

Certain exemplary embodiments will now be described to provide an overall understanding of the principles of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Additionally, to the extent that linear or circular dimensions are used in the description of the disclosed devices and methods, such dimensions are not intended to limit the types of shapes that can be used in conjunction with such devices and methods. A person skilled in the art will recognize that an equivalent to such linear and circular dimensions can easily be determined for any geometric shape. Further, in the present disclosure, like-numbered components of the embodiments generally have similar features. Still further, sizes and shapes of the devices, and the components thereof, can depend at least on the anatomy of the subject in which the devices will be used, the size and shape of components with which the devices will be used (e.g., the allograft or autograft), and the methods and procedures in which the devices will be used.

Described herein are devices and methods for reinforcing a tissue graft or other implant that can provide a number of advantages, including the ability to reinforce a bone plug of any quality. For example, a reinforcing insert according to the teachings of the present invention can be used preventatively when the quality of a bone plug is in question or known to be inferior. In such an instance, an insert can be installed in a through-hole of the bone plug to distribute forces from a surgeon pulling on a suture extending through the through-hole when positioning a graft or other implant. The insert can better distribute these loads because it contacts the sidewalls of the bone plug through-hole over a greater area than the suture alone. Any installation forces can be distributed over the larger area and the pressure applied to the bone plug at any one point can be decreased. The lower pressure can decrease the likelihood of the bone plug failing due to suture pull-through. Moreover, in some embodiments the insert can be shaped such that it can be inserted into a bone plug through-hole in a manner that maintains a desired through-hole diameter and does not introduce new failure points by reducing the cross sectional area of the bone plug adjacent to the through-hole.

Figure 1:
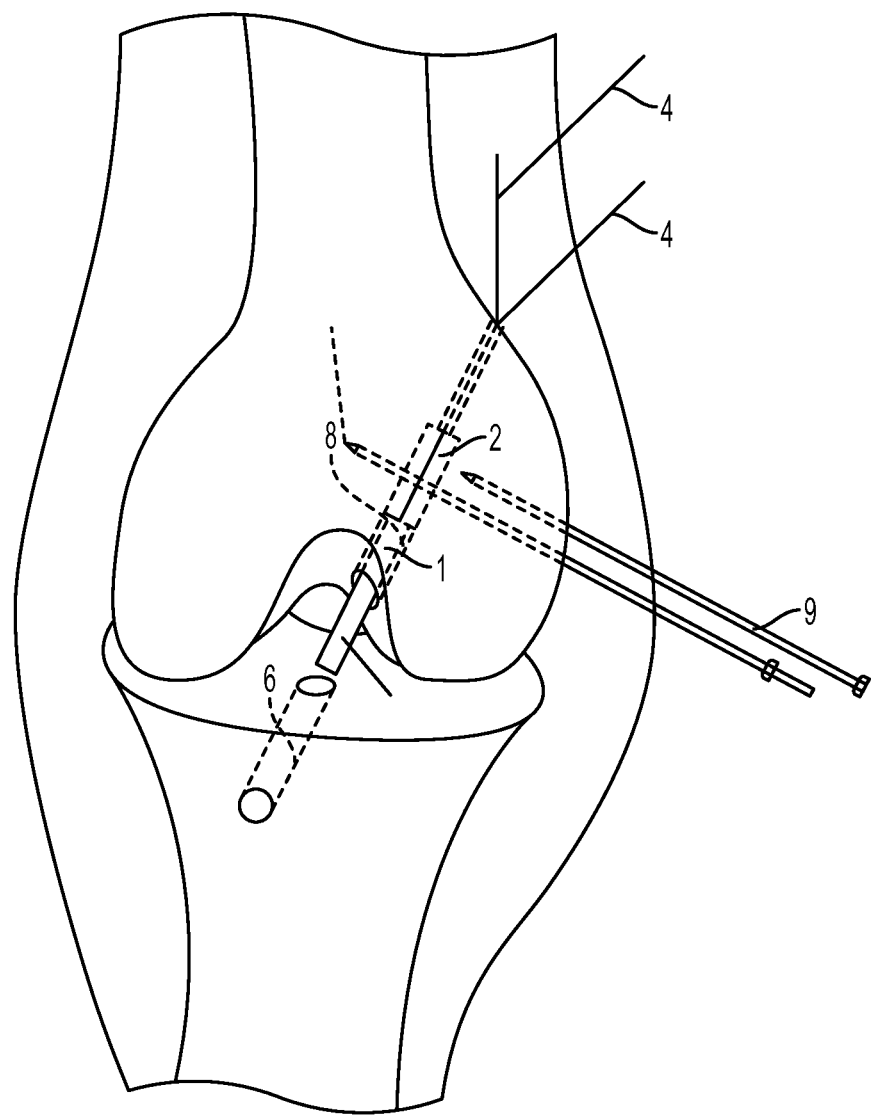
FIG. 1 illustrates a patient's knee during a ligament repair procedure.
Figure 2C:
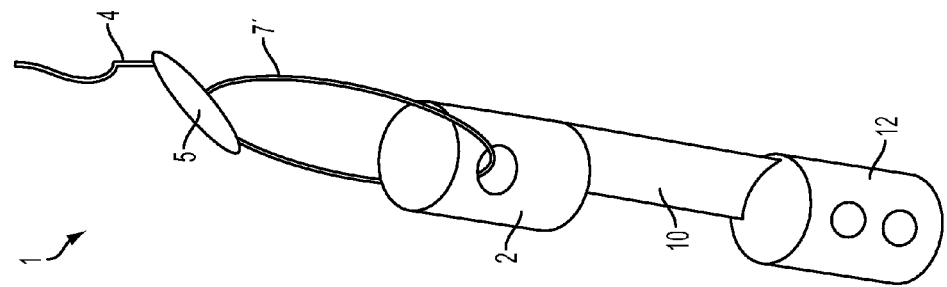
FIG. 2C illustrates another embodiment of an implant including a pull suture.
Figure 2B:
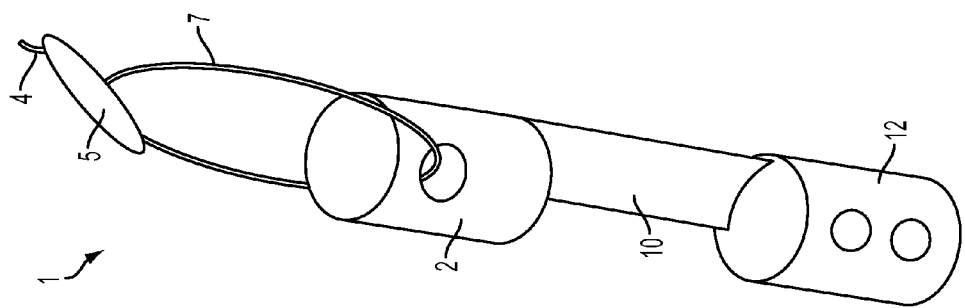
FIG. 2B illustrates an alternative embodiment of an implant including a pull suture.
Figure 2A:
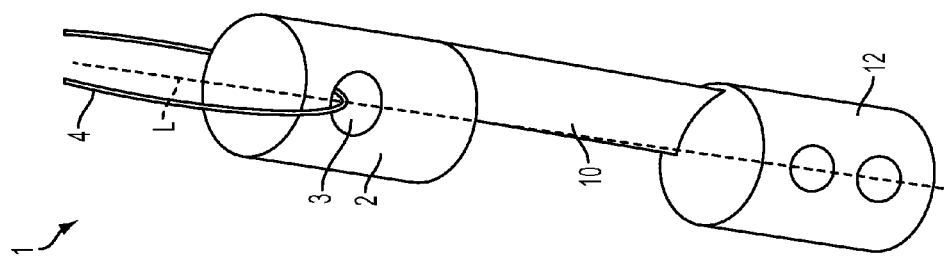
FIG. 2A illustrates one embodiment of an implant including a pull suture.

Implantation of an ACL graft can generally require preparation of the patient's knee, as shown in FIG. 1. The surgeon can incise the patient at the knee to expose the knee joint. After the knee joint has been exposed, the surgeon can remove the damaged soft tissue and create tibial and femoral bone tunnels 6, 8, which can receive the bone plug portions of an implant 1, such as a BTB graft. Once the knee is properly prepared for the implant, the surgeon can thread a suture 4 through a through-hole 3 in a leading bone plug 2, as shown in FIGS. 2A-C. If the implant 1 is supplied without a through-hole in the leading bone plug 2, a surgeon can drill, punch, or otherwise form an appropriately sized through-hole in the bone plug 2 for this purpose. Any number of suture configurations can be used to secure the suture 4 to the bone plug 2. For example, FIG. 2A shows a straight pull configuration of the suture 4 where the suture is threaded through the bone plug through-hole 3 and the two free ends can be manipulated by a surgeon. FIGS. 2B and 2C show alternative embodiments where the suture 4 includes a cortical button 5 around which the suture is looped and knotted so as to create one or more suture loops 7, 7' extending from the button 5, as well as a free end of the suture 4 that can be used to pull the implant 1 into position. The suture loops 7, 7' extending below the cortical button 5 and through the through-hole 3 can have an adjustable length (as shown in FIG. 2B, loops 7) or a fixed length (as shown in FIG. 2C, loops 7'), depending on how the suture is threaded through and knotted about the cortical button. Exemplary cortical buttons and suture threading configurations are disclosed in U.S. patent application Ser. No. 14/340,683, filed on Jul. 25, 2014, and entitled "Adjustable Graft Fixation Device," as well as U.S. patent application Ser. No. 13/793,514, filed on Mar. 11, 2013, and entitled "Implant Having Adjustable Filament Coils," and U.S. patent application Ser. No. 14/103,167, filed on Dec. 11, 2013, and entitled "Implant Having Filament Limbs of an Adjustable Loop Disposed in a Shuttle Suture." The disclosures of each of these applications are hereby incorporated by reference in their entirety as if their entire contents were reproduced herein.

As shown in FIG. 1, the implant 1 can be positioned within a patient's body by guiding the suture 4 through the tibial tunnel 6 and the femoral tunnel 8. Once the suture 4 has been threaded through the bone tunnels, the surgeon can use the suture 4 to pull the implant 1 into place (e.g., to a position in which the bone plug 2 rests in the femoral bone tunnel 8, the bone plug 12 rests in the tibial bone tunnel 6, and the implant 1 extends between the femur and tibia). When the surgeon has properly implanted the BTB graft or other implant 1 in the patient's knee, the bone plug ends of the graft can be secured within the tunnels such that they are fixed relative to the tibia and femur (e.g., using cross pins 9 or other fixation elements). While reference is made herein to a BTB graft commonly utilized in ACL reconstruction, the bone plug insert can be readily used in reconstruction of other soft tissue as well.

A BTB allograft for an ACL reconstruction procedure can be harvested from a cadaver by a technician prior to the reconstruction procedure. The cadaver can be screened for any potential diseases to avoid infecting the patient undergoing the reconstruction procedure. While a cadaver can be screened for disease, the quality of the BTB allograft can still vary significantly based upon the age and/or health of the cadaver. As a result, the quality of the bone plugs of the BTB allograft may not be known. A technician can harvest a BTB graft by cutting a portion of the patellar tendon 10 that includes bone plugs 2, 12 from the tibia and patella at either end. Other known allograft tissue can include the Achilles, tibialis and peroneus longus tendons, as well as the anterior cruciate ligament itself. The bone plugs 2, 12 can have a generally cylindrical shape extending along a longitudinal axis L and can have at least one through-hole formed therein that extends through the bone plug in a direction perpendicular to the longitudinal axis. Just as the bone plugs provided for herein can be used in other procedures, other configurations of grafts can also be used in conjunction with the disclosures provided for herein without departing from the spirit of the present disclosure. The disclosures pertaining to the size and shape of grafts and plugs in no way limit the applicability of the present teachings. In particular, the disclosures pertaining to a bone plug reinforcing insert can be applied to any number of grafts, plugs, or other related types of implants.

After a graft has been harvested, a technician can process the graft for packaging and use. Processing of the graft can include cleaning the graft and freezing it in liquid nitrogen for preservation and sterilization. Other processing and sterilization techniques can be used, including treating the graft with low dose irradiation and/or chemical disinfectants or any other processing and sterilization techniques known in the art.

As discussed above, the surgical procedure for ACL reconstruction can include drawing an implant 1 into a bone tunnel by pulling on a suture coupled to the implant. For example, the bone plug 2 can be drawn through the tibial and femoral bone tunnels 6, 8 by pulling on the suture 4, as shown in FIGS. 2A-2C. If the bone plug 2 is of poor initial quality, or has been degraded by irradiation or other sterilization techniques performed during processing, the leading suture 4 (FIG. 2A) or loops 7, 7' (FIGS. 2B, 2C, respectively) can pull straight through the bone plug 2 during implantation. The risk of the suture pulling through the bone plug can be present even with high quality bone grafts due to the concentrated forces applied to the bone plug by the suture. That is, the pulling force applied to the suture is typically transmitted to the bone plug over a small contact area, thereby creating a large amount of pressure at the point of contact.

Figure 4:
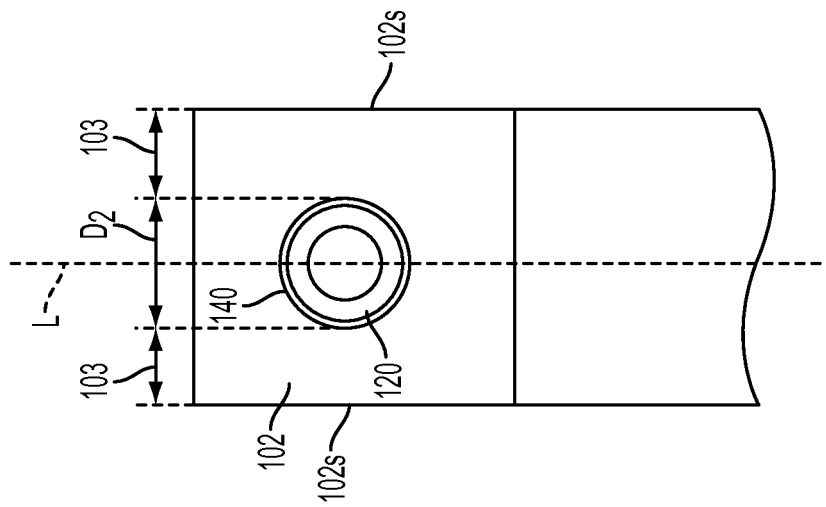
FIG. 4 is a side-view of one embodiment of an implant including the reinforcing insert of FIG. 3.
Figure 3:
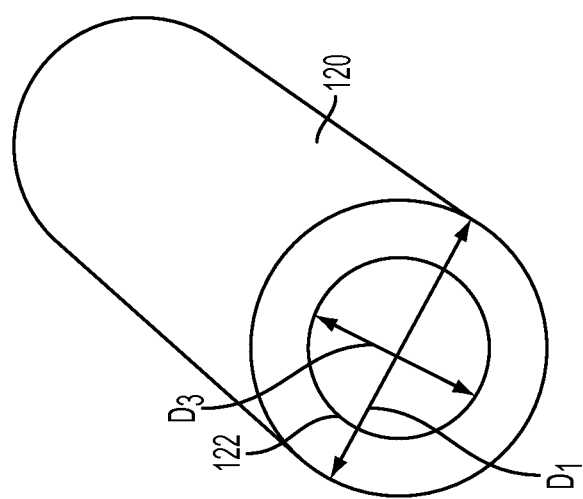
FIG. 3 is an isometric view of one embodiment of a reinforcing insert.

One solution to this problem can be to distribute the loading forces applied to the bone plug over a larger contact area, thereby reducing the pressure on the bone plug. FIG. 3 illustrates one embodiment of a bone plug reinforcing insert 120 for this purpose. The bone plug insert 120 can have a generally cylindrical shape and can include a through-hole 122 extending therethrough. The cylindrical bone plug insert 120 can be positioned within a through-hole 140 of a bone plug 102, as shown in FIG. 4. The cylindrical bone plug insert 120 can be sized so that it can be inserted within the bone plug through-hole 140 with no additional preparation to the bone plug. Sizing the cylindrical bone plug insert 120 to have an outer diameter $D_1$ about equal to the diameter $D_2$ of the through-hole 140 of the bone plug 102 can maximize the amount of material present in the bone plug 102 and thereby maintain the structural integrity of the bone plug 102.

In some embodiments it can be desirable to maintain at least a minimum value for a diameter $D_3$ of the bone plug insert through-hole 122. For example, it may be desirable for the diameter $D_3$ to be at least equal to a diameter of the through-hole 140 that would be formed in the bone plug in a case where no insert 120 is used. This diameter can be determined, for example, by a minimum diameter necessary to pass one or more suture loops through the bone plug through-hole 140. In such instances, the insert 120 can be constructed such that its inner diameter $D_3$ (i.e., the diameter of the bone plug insert through-hole 122) is equal to or greater than the minimum value. Doing so necessarily increases the outer diameter $D_1$ of the insert 122, however, and requires that the diameter of the bone plug through-hole 140 be larger than it might otherwise have to be if no insert were used. Forming a larger diameter bone plug through-hole 140 removes additional material from the bone plug 102, which in turn can weaken the bone plug and increase the likelihood of failure in the area surrounding the through-hole 140 due to the decreased amount of material. This can be especially true in the often-narrower width direction extending perpendicular to a longitudinal axis L of the bone plug 102 (e.g., the portions 103 extending between the sidewalls 102s of the plug 102 and the outer edge of the through-hole 140, as shown in FIG. 4). However, the use of an insert 120 can remain advantageous even despite the weakening that can occur when a larger bone plug through-hole 140 is formed to accommodate the outer diameter $D_1$ of the insert 120.

The bone plug insert 120 can be inserted into the bone plug 102 in a variety of different manners, depending at least in part on the materials being used, the type of procedure being performed, and user preference. By way of non-limiting example, the bone plug insert 120 can be installed into the bone plug through-hole 140 prophylactically, for instance if the bone plug is known to be of lesser quality that might not withstand installation forces. In some embodiments, the insert 120 can even be installed after a suture 4 has torn through the bone plug 102. In such an embodiment, use of a bone plug reinforcing insert 120 can allow a graft to be used when it would otherwise normally be discarded. A number of other methods known to those skilled in the art for inserting a material into a bone plug can also be used.

The timing of when the bone plug insert 120 is inserted into the bone plug 102 can also vary. In some embodiments, once the cylindrical bone plug insert 120 has been installed within the bone plug 102, a surgeon can thread the suture 4 through the reinforced hole and continue with the implantation procedure. Alternatively, a suture 4 can first be threaded through the cylindrical bone plug insert 120 and the bone plug 102, and then the cylindrical bone plug insert 120, can be inserted into the bone plug 102.

In some embodiments a suture may be disposed in a bone plug before a bone plug insert is introduced. This can include embodiments such as those illustrated in FIGS. 2B and 2C in which the suture ends are tied and thus may not be easily accessible to thread the suture through the bone plug after a bone plug insert is introduced. A bone plug insert that is configured to allow an internal surface of the insert to be accessed directly from the through-hole of the bone plug can be utilized in such instances. One exemplary embodiment of such a bone plug insert is the bone plug insert 220 illustrated in FIG. 5.

Figure 6:
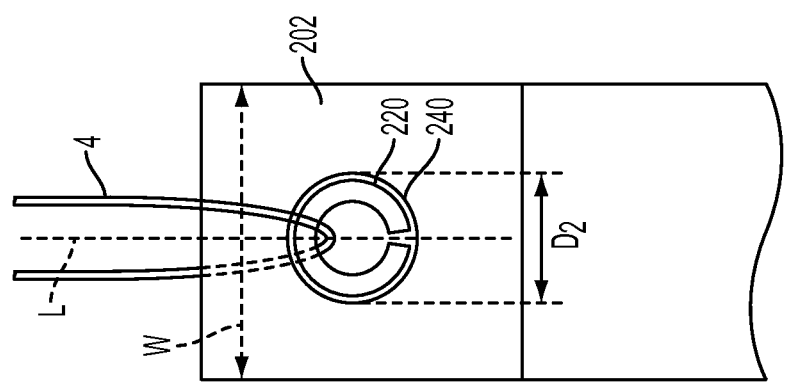
FIG. 6 is a side-view of one embodiment of an implant including the reinforcing insert of FIG. 5.
Figure 5:
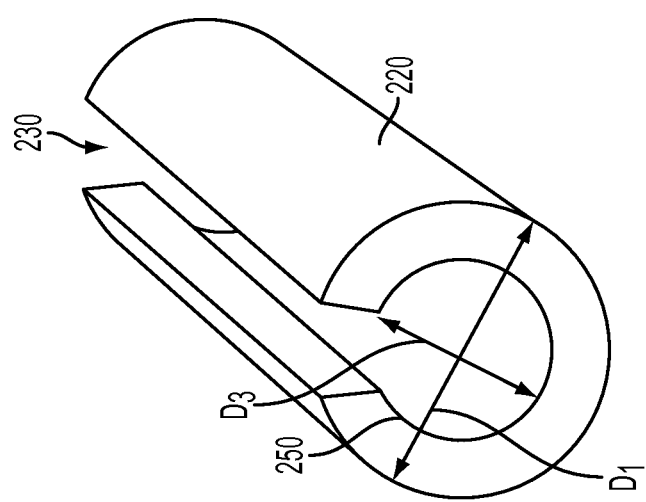
FIG. 5 is an isometric view of an alternative embodiment of a reinforcing insert.

As shown in FIG. 5, the bone plug reinforcement insert 220 can have a cylindrical shape with a slit 230 creating a "C" shaped cross section. The slit 230 can allow the insert 220 to be passed over a suture 4 and subsequently positioned in a bone plug though-hole 240 without the need to remove the suture 4 or untie any knots. The insert 220 can alternatively be inserted into a bone plug 202 prior to threading a suture though the insert. After passing the insert 220 over a suture and positioning it within a bone plug through-hole 240, the insert can be rotated such that the slit faces away from the direction of loading (e.g., the upward direction, or the direction that the suture 4 is extending, in FIG. 6). This can prevent the suture 4 from slipping through the slit during implantation and coming into contact with the bone plug 202.

As mentioned above, when utilizing the bone plug inserts 120 and 220, surgeons may decide to increase the diameter of the through-hole 140, 240 formed in the bone plug 102, 202 so that an inner through-hole 250 of the insert can have a desired diameter $D_3$, such as approximately the same diameter of a through-hole that would be formed in the bone plug 202 if no insert were being used. Alternatively, surgeons may opt to leave the diameter of the through-hole 140, 240 formed in the bone plug 102, 202 the same size as would be used without an insert, and thus use an insert with an inner through-hole 250 that has a smaller diameter $D_3$ than would normally be formed in the bone plug 202 if no insert were used.

In instances in which surgeons desire a particular diameter for the through-hole remaining after positioning of any insert (e.g., a particular desired diameter for the inner through-hole 250 of the insert 220), the surgeon will typically increase the diameter of the through-hole of the bone plug (e.g., the diameter $D_2$ of through-hole 240). However, it can be detrimental to remove additional material from a bone plug in this manner because doing so can reduce the cross-sectional area of bone surrounding the through-hole, thereby introducing additional failure points and increasing the likelihood of bone plug failure. Moreover, it can be particularly detrimental to remove additional material in areas where the bone plug is already at its thinnest, such as in a width direction W extending perpendicular to the longitudinal axis L of the bone plug. The bone plug is typically thinner in this direction than it is along the longitudinal axis L due to its generally cylindrical and elongate shape. As a result, in some instances it can be desirable to maintain (i.e., not increase) a diameter of a bone plug through-hole in a width direction that extends perpendicular to a longitudinal axis of the bone plug so as to maximize the amount of bone material surrounding the through-hole. It can be difficult to reconcile the competing goals of providing a bone plug reinforcing insert that does not restrict the diameter of the final through-hole that receives sutures but also does not remove additional material from the bone plug at its weakest points (i.e., where the material thickness is already less than at other locations of the bone plug).

Figure 7A:
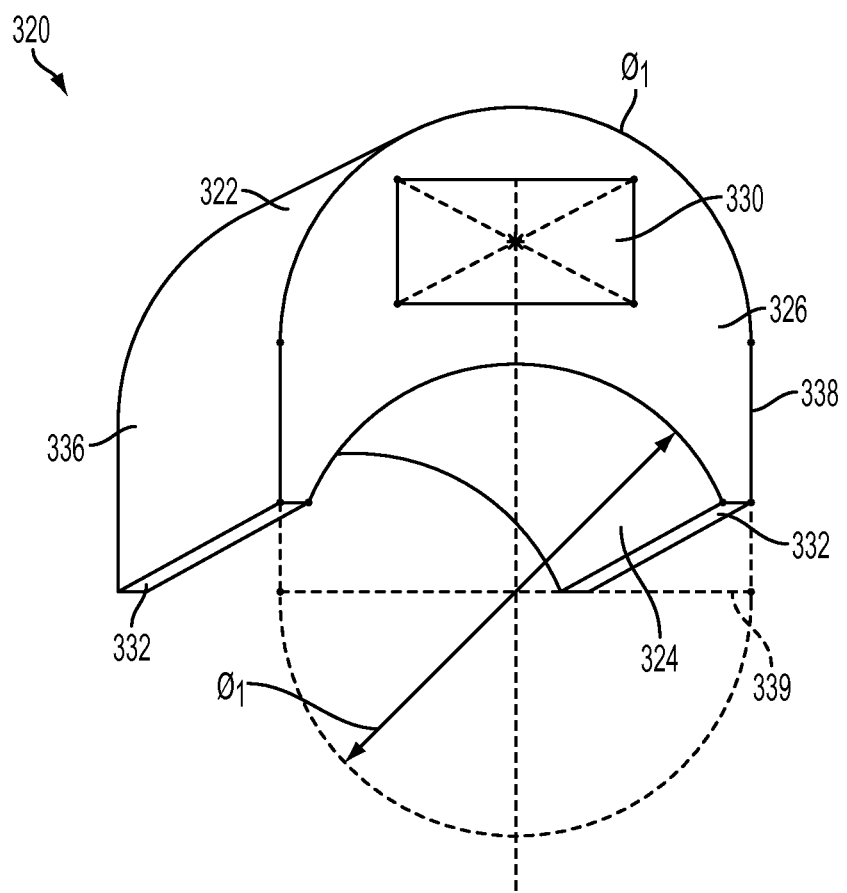
FIG. 7A is a front isometric view of another alternative embodiment of a reinforcing insert.
Figure 7B:
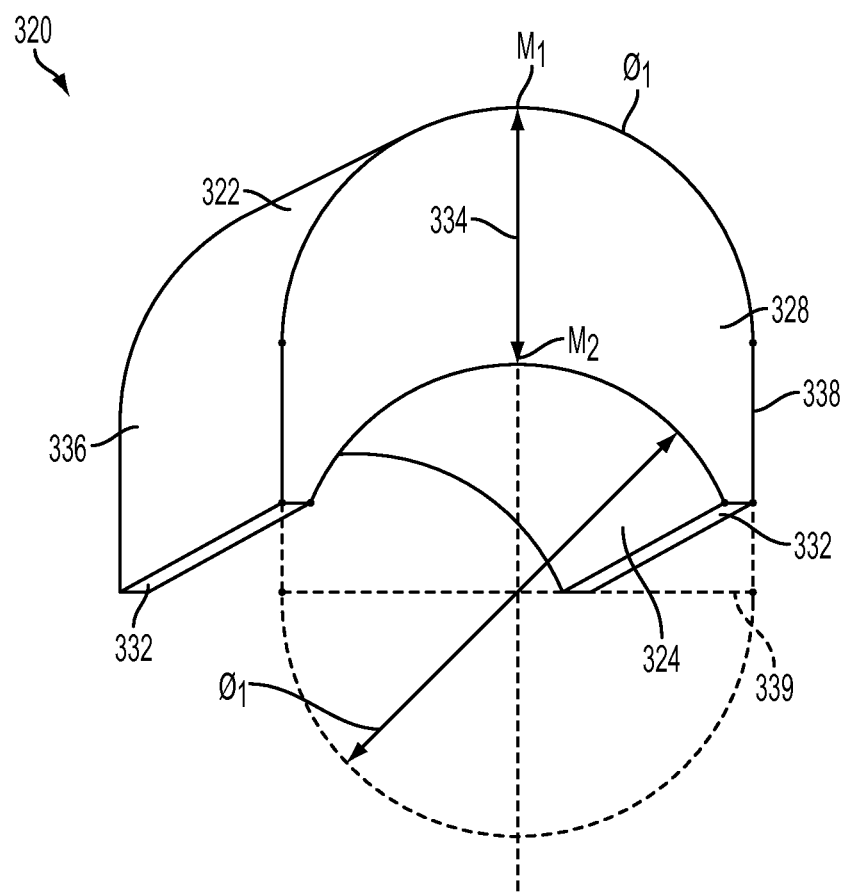
FIG. 7B is a rear isometric view of the reinforcing insert of FIG. 7A.
Figure 8C:
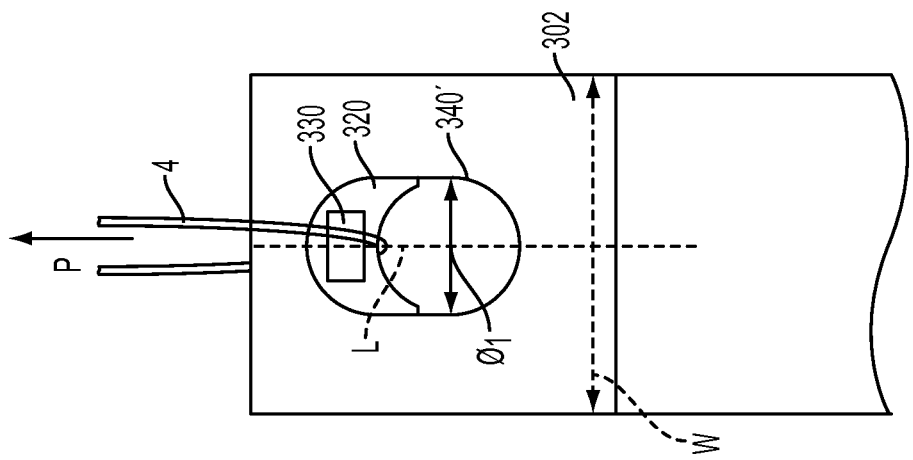
FIG. 8C is a side view of the implant of FIGS. 8A-8B including the reinforcing insert of FIG. 7.
Figure 8B:
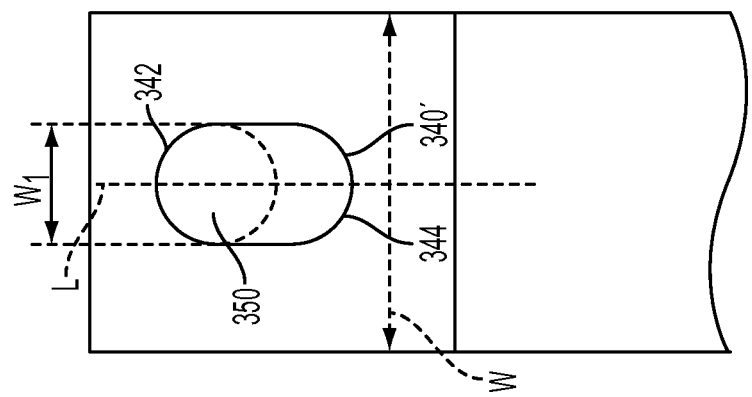
FIG. 8B is a side view of a second step for preparing an implant having a reinforced bone plug through-hole.
Figure 8A:
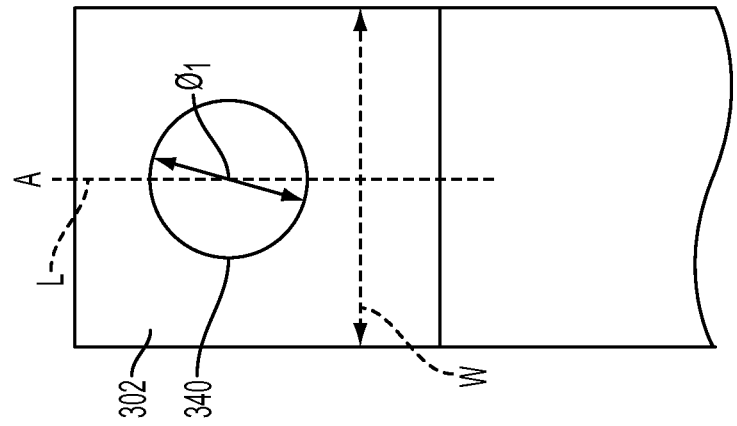
FIG. 8A is a side view of a first step for preparing an implant having a reinforced bone plug through-hole.

FIGS. 7A and 7B illustrate one embodiment of a bone plug insert 320 that can address the competing goals mentioned above and maintain both a desired diameter of a final bone plug through-hole and an amount of bone surrounding the bone plug through-hole. The bone plug insert 320 of FIGS. 7A and 7B can therefore provide surgeons with the benefits of decreased loading stresses on the upper portion of the bone plug through-hole 340 of the bone plug 302 (as shown in FIGS. 8A-8C), maintaining an initial diameter of the bone plug through-hole 340, and maintaining the amount of bone plug material in the width direction W. In the illustrated embodiment, this is accomplished by enlarging the bone plug through-hole 340 in a length direction (i.e., parallel to a longitudinal axis L of the cylindrical bone plug 302) to accommodate the insert 320 while not removing additional bone in the width direction W (i.e., perpendicular to the longitudinal axis of the cylindrical bone plug 302) of the through-hole 340, thereby creating an oblong-shaped through-hole (i.e., a through-hole having an oblong cross-section) into which the insert 320 can be inserted.

The bone plug insert 320 of FIGS. 7A and 7B can have a proximal face 326, a distal face 328, a convex upper surface 322, and a concave lower surface 324. The convex upper surface 322 and the concave lower surface 324 can extend between the proximal face 326 and the distal face 328. The convex upper surface 322 and the concave lower surface 324 can be coupled to one another via connecting surfaces 332 that can extend between the proximal and distal faces 326, 328 of the insert. In some embodiments, the connecting surfaces 332 can be formed by chamfering an edge created by the intersection of the convex upper surface 322 and the concave lower surface 324. In addition, in certain embodiments the insert 320 can include first and second sidewalls 336, 338 extending between the proximal and distal faces 326, 328, and also serving to connect the convex upper surface 322 to the concave lower surface 324. The sidewalls 336, 338 can have a different radius of curvature than the convex upper portion 322 or the concave lower portion 324, or can have a flat (i.e., planar) profile. In embodiments where a distance 334 between the convex upper surface 322 and the concave lower surface 324 is large, first and second sidewalls 336, 338 can connect the upper and lower surfaces without increasing the overall width 339 of the insert 320 (i.e., maintaining the width 339 at or below the diameter $\o_1$). In some instances, the convex upper surface 322 and the concave lower surface 324 can encompass the sidewalls 336, 338. Further, in some embodiments the convex upper surface 322 and the concave lower surface 324 can contact each other directly such that the connecting surfaces 332 are the location at which the convex upper surface 322 meets the concave lower surface 324 without a formed chamfered edge or the like.

The bone plug insert 320 can increase the amount of pulling force that a bone plug can successfully bear. After installation in a through-hole of a bone plug (e.g., as shown in FIG. 8C), a suture disposed in the through-hole can contact the bone plug insert 320 on the concave lower surface 324, which in turn can redistribute a pulling force across a larger surface area of the bone plug 302 via the concave upper surface 322 that abuts against an upper surface of the bone plug through-hole 340'.

The bone plug insert 320 can also include one or more features formed thereon that are configured to allow coupling of the bone plug insert 320 to an insertion tool, or to facilitate grasping of the insert 320 by a surgeon or other user. For example, the proximal and/or distal faces 326, 328 can include any number of surface features formed thereon, such as one or more tabs or protrusions, one or more indentations, etc. that can facilitate grasping of the insert by hand and/or with one or more tools. These features, if they protrude from the surfaces 326, 328, can be configured to snap off or otherwise be removed after the insert 320 has been positioned within a bone plug through-hole. In other embodiments, for example, the proximal and/or distal face 326, 328 of the bone plug insert can include a cavity 330, such as a drafted pocket, that can be used to accept a portion of an insertion tool used to position the insert 320 within a bone plug through-hole. The cavity can have any of a variety of shapes and sizes but, in some embodiments, the cavity can have a rectangular shape with a height and a width that are between about 0.5 millimeters and about 1.0 millimeter. The depth of the cavity can vary as well, and can be as shallow as 0.5 millimeters or can be formed as a through-hole extending between the proximal and distal faces 326, 328.

The bone plug 302, as shown in FIGS. 8A-8C, can receive the bone plug insert 320 in a modified oblong through-hole 340'. As noted above, the bone plug 302 can have a circular or substantially circular though-hole 340 created by a technician during an initial processing of the graft, or the through-hole 340 can alternatively be created by a surgeon at the time of the implantation procedure. The through-hole 340' can be made by modifying the substantially circular through-hole 340 of the bone plug 302 such that it has a non-circular or substantially non-circular shape, such as an oblong or elliptical shape opening (i.e., a cross-section of the opening is oblong in shape). In the embodiment shown in FIG. 8C, for example, the modified through-hole 340' can have a diameter $ø_1$ at an upper end and a lower end thereof, with a constant width $W_1$ therebetween (the width $W_1$ can be equal to the diameter $ø_1$). By not increasing the diameter of the modified through-hole 340' in the width direction W (i.e., the left-right direction in FIGS. 8B and 8C), the bone plug can maintain the amount of material surrounding the modified through-hole 340' at its thinnest points and provide for removing excess material only from an upper or lower surface of the through-hole 340 where the thickness of the surrounding bone plug is typically greater. Modifying the through-hole 340 in this manner can permit the use of the insert 320 without restricting the diameter of the reinforced through-hole that receives sutures or introducing additional failure points for the bone plug. While the modified through-hole 340' is described above as having identical diameters at its upper and lower ends, in other embodiments the modified through-hole 340' can have one diameter at its upper end and a different diameter at its lower end. In such embodiments, the convex upper surface 322 and the lower concave surface 324 of the insert 320 can be shaped such that their radii of curvature match the radii of curvature of the upper and lower portions of the modified through-hole 340', respectively.

The diameters or radii of curvature of the upper and lower portions of the bone plug through-hole 340' can be any of a variety of sizes, depending, at least in part, on the size of the bone plugs, sutures to be passed through the bone plugs, and the type of procedure being performed. In some embodiments, for example, the diameter $ø_1$ of the modified through-hole 340' can be in a range of about 1 millimeters to about 3 millimeters. In certain embodiments, the diameter $ø_1$ of the modified through-hole 340' can be about 2 millimeters. The length of the through-hole can be dictated, at least in part, by the size of the bone plug employed and the type of procedure being performed, but in some embodiments can be in a range of about 1 millimeter to about 8 millimeters.

The bone plug insert 320 can be sized such that it can be inserted into the modified through-hole 340' so that the convex upper surface 322 mates with or abuts against the upper surface 342 of the modified through-hole. Further, in some embodiments like the one illustrated in FIG. 8C, once the insert 320 is installed, a circular reinforced through-hole can remain that has approximately the same diameter $ø_1$ as the initial through-hole 340. This can be accomplished because the lower portion 344 of the modified through-hole 340' can have the same diameter or radius of curvature as the concave lower surface 324 of the bone plug insert 320. Alternatively, the convex upper surface 322, the concave lower surface 324, and the upper and lower portions 342, 344 of the modified through-hole 340' can have different radii of curvature. In any case, the radii of curvature of the upper surface of the through-hole 340' and the upper convex surface 322 can match, as can the radii of curvature of the lower surface of the through-hole 340' and the lower concave surface 324. Moreover, in some embodiments the bone plug insert 320 can have a particular height, i.e., a particular distance 334 extending between midpoints $M_1$ of the upper convex surface 322 and $M_2$ of the lower concave surface 324 as measured along the proximal and/or distal faces 326, 328. In some embodiments, for example, this distance can also be in a range between about 0.5 millimeter and about 1.5 millimeters, and can be about 1 millimeter in certain embodiments.

As mentioned above, the radii of curvature of the upper convex surface 322 and the lower concave surface 324 can match the radii of curvature of the upper portion of the through-hole 340' and the lower portion of the through-hole 340', respectively. Accordingly, in certain embodiments the radii of curvature of the upper convex surface 322 and the lower concave surface 324 can be in a range of about 0.5 millimeters to about 1.5 millimeters. In some embodiments, the radii of curvature of these surfaces can be about 1 millimeter. The insert 320 can have any of a variety of lengths. For example, in some embodiments the insert 320 can be as long as the through-hole 340', i.e., as wide as the bone plug 302 in the width direction W. In other embodiments, however, the insert 320 can have a length extending between the proximal and distal faces 326, 328 that is shorter than a length of the through-hole 340', such that the insert is recessed from an outer surface of the bone plug 302 once positioned within the through-hole 340'. In some exemplary embodiments, a length of the insert can be in the range of about 2 millimeters to about 20 millimeters, and in one exemplary embodiment the length can be about 10 millimeters.

The bone plug insert 320 can be formed from any of a variety of biocompatible materials known in the art. Exemplary materials suitable for use in forming the insert 320 can include stainless steel, titanium, and other biocompatible metals. Non-metallic materials, such as various biocompatible polymers, including polyether ether ketone (PEEK), can also be used. A selected material should be able to withstand the forces experienced during installation and use of a tissue graft, so that sutures are incapable of pulling through the insert in the same manner that can be experienced when using only a bone plug.

As shown in FIG. 8C, in use, such as during positioning of an implant in a patient, a suture 4 can contact the concave lower surface 324 of the insert 320. Upward forces in the direction of arrow P can be applied to the suture 4 and transferred to the bone plug 302 through the insert 320. The insert 320 can distribute the forces over the surface area of the insert 320, and consequently can transfer the forces to the bone plug 302 over the surface area of contact between the upper convex surface 322 and the upper portion 342 of the through-hole. This distribution over a larger surface area can lower the pressure applied to the bone plug 302 and the stress present in the bone plug 302 at any one location. The better distribution of force can allow a surgeon to pull the bone plug 302 through the femoral and tibial tunnels 6, 8 to properly position the implant 1 with a decreased risk of bone plug 302 failure.

Figure 9:
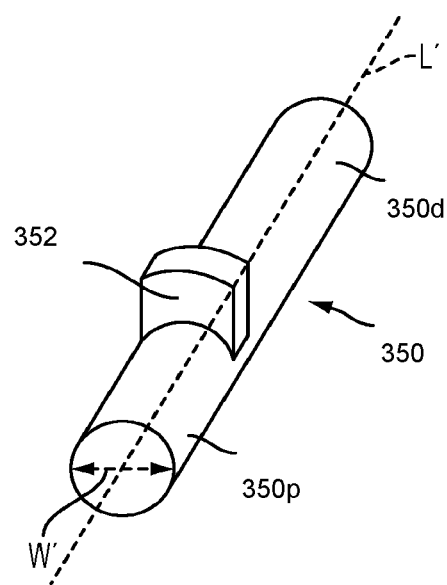
FIG. 9 is an isometric view of one embodiment of a tool that can be used to form the oblong through-hole of FIG. 8B.

In order to prepare the bone plug 302 for the bone plug insert 320, the symmetrical (e.g., circular) through-hole 340 can be expanded into the oblong shape of the through-hole 340' in a variety of manners. In some embodiments, the through-hole 340 can be modified using a punch 350, as shown in FIG. 9, or another similarly-purposed tool or instrument. The punch 350 can be an elongate cylindrical tool with a longitudinal axis L' extending between a proximal end 350p and a distal end 350d. The punch can include a protrusion 352 extending perpendicular to the longitudinal axis L' from an outer surface thereof. The protrusion 352 can extend along the majority of a length of the tool 350 or, as shown in FIG. 9, can extend along a relatively short distance. The punch 350 can be manufactured out of any suitable material capable of forming bone and can be packaged with the insert or separate therefrom. Exemplary materials can include metals, such as stainless steel or titanium, as well as suitable rigid polymers, such as PEEK.

Initially, the bone plug 302 can be prepared for installation by following the steps illustrated in FIGS. 8A-C. The bone plug 302, as shown in FIG. 8A for example, can have a through-hole 340 which can be used to receive a suture 4 (shown in FIG. 8C), having a diameter $\varnothing_1$ in the range of about 1 millimeter to about 3 millimeters. Referring to FIG. 8B, the punch 350 can be inserted within the through-hole 340 and advanced to create the modified through-hole 340' for the insert 320. As noted above, the diameter of the tool 350 in the width direction W', and subsequently the diameter of the through-hole 340' in the width direction W, can be maintained during this procedure. A proximal portion of the tool 350, which can have the same or a slightly smaller diameter than the through-hole 340, can be inserted into the bone plug through-hole 340.

A surgeon or technician can push the punch 350 through the bone plug through-hole 340 such that the protrusion 352 forms the oblong shape of the modified bone plug through-hole 340'. Advancing the punch 350 through the bone plug through-hole 340 can be done by hand or using a tool, such as by using a mallet or a hammer. The punch 350 can be advanced through the through-hole 340 so that the radially extending protrusion 352 removes additional material to create the oblong-shaped modified through-hole 340'. The punch 350 can be advanced through the bone plug linearly without rotation so that the desired geometry of the modified through-hole 340' is attained. A person skilled in the art will recognize a variety of other geometries that can be formed in view of the disclosures herein, either using the punch 350, a punch having a different configuration, or using other techniques for forming and/or modifying through-holes. In some embodiments, this procedure can be completed just after the bone plug is harvested from a cadaver or, in other embodiments, can be performed by a surgeon during an implantation procedure. In still other embodiments, the modified through-hole 340' can be created using other known methods, for example using a drill passed through the bone plug at offset locations.

Once the modified through-hole 340' has been formed, as shown in FIG. 8B, a surgeon can install the bone plug insert 320. The bone plug insert 320 can be placed in the modified through hole in a variety of manners, including by hand or with a tool. In embodiments that employ an insertion tool, the insert 320 can be coupled to the tool via, for example, a cavity 330 formed in the bone plug insert 320. One or more suture loops or lengths of suture can be threaded through the through-hole 340' either before or after insertion of the insert 320 within the through-hole. The insert 320 can be positioned such that the one or more suture loops contact the insert, rather than the bone plug, when a surgeon applies a pulling force to the suture (e.g., such as a force on the suture 4 in the direction P shown in FIG. 8C).

As mentioned above, the bone plug reinforcing inserts and associated tools described herein can be formed from any of a variety of biocompatible materials. Suitable biocompatible materials can include, for example, metals such as stainless steel and titanium. Other materials, such as polymers, can also be used, provided the material can withstand the forces that are experienced during installation and use. Further, in certain embodiments particular components can be made from different materials. For example, a medical driver tool can be made from one material while an insert or other component can be made from a different material.

While the bone plug reinforcing inserts are typically left implanted within a patient, it is contemplated that the insert and other tools and associated devices described herein can be designed for multiple uses and can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present invention.

Preferably, the bone plug reinforcement inserts and the associated accessories described herein will be processed before surgery. First, a new or used insert or accessory can be obtained and, if necessary, cleaned. The insert or accessory can then be sterilized. In one sterilization technique, the insert or accessory can be placed in a closed and sealed container, such as a plastic or TYVEK bag. The container and its contents can then be placed in a field of radiation that can penetrate the container, such as gamma radiation, x-rays, or high-energy electrons. The radiation can kill bacteria on the instrument and in the container. The sterilized insert or accessory can then be stored in the sterile container. The sealed container can keep the insert or accessory sterile until it is opened in the medical facility. In other embodiments, sterilization can be performed using any number of ways known to those skilled in the art including beta or gamma radiation, ethylene oxide, steam, or a liquid bath (e.g., cold soak).

All papers and publications cited herein are hereby incorporated by reference in their entirety. One skilled in the art will appreciate further features and advantages of the invention based on the above-described embodiments. Accordingly, the invention is not to be limited by what has been particularly shown and described, except as indicated by the appended claims.

What is claimed is:

1. An implant, comprising:
   a proximal end portion formed of bone and having a through-hole formed therein;
   a distal end portion formed of bone;
   a tendon coupled to the proximal end portion distal to the through-hole and extending between the proximal end portion and the distal end portion; and
   a reinforcing insert disposed in the through-hole, the insert comprising:
      a proximal face;
      a distal face opposed to the proximal face;
      a first upper surface extending between the proximal and distal faces, the upper surface having an upward-facing generally convex shape that abuts against at least a portion of a sidewall of the through-hole; and
      a second lower surface extending between the proximal and distal faces, the lower surface being opposed to and disposed below the first upper surface, the lower surface having at least a portion with a downward-facing generally concave shape, and the second lower surface and portions of the sidewall of the through-hole not abutted by the first upper surface forming a reinforced through-hole of the implant,
   wherein a cross-section of the through-hole has a non-circular shape and a cross-section of the reinforced through-hole has a circular shape.

2. The implant of claim 1, wherein a radius of curvature of the first upper surface of the reinforcing insert associated with the generally convex shape is approximately equal to a radius of curvature of the portion of the sidewall of the through-hole against which the first upper surface abuts.

3. The implant of claim 1, wherein a radius of curvature of the at least portion of the second lower surface of the reinforcing insert associated with the generally concave shape is approximately equal to a radius of the through-hole.

4. The implant of claim 1, wherein the distance between a midpoint of the convex surface and a midpoint of the concave surface is about 1 millimeter.

5. The implant of claim 1, wherein at least one of the proximal and distal faces has a cavity formed therein for receiving an insertion tool.

6. The implant of claim 1, further comprising a suture disposed in the reinforced through-hole.

7. The implant of claim 1, wherein the tendon, the proximal end portion, and the distal end portion are aligned along a longitudinal axis of the implant; and
   wherein the tendon is coupled to a distal-most end of the proximal end portion and a proximal-most end of the distal end portion.

8. A reinforced bone plug, comprising:
   a bone plug having a substantially cylindrical shape with a proximal end and a distal end, and a through-hole extending transversely across a longitudinal axis of the bone plug; and
   an insert movable relative to the bone plug and positioned within the through-hole such that a proximally-facing convex surface of the insert abuts against at least a portion of a sidewall of the through-hole and a second surface of the insert that includes at least a distally-facing portion that is concave intersects at least a second portion of the sidewall of the through-hole to define a reinforced through-hole in the bone plug;
   wherein a cross-section of the through-hole is oblong and a cross-section of the reinforced through-hole is a substantially circular.

9. The reinforced bone plug of claim 8, wherein a radius of curvature of the convex surface is substantially equal to a radius of curvature of the portion of the sidewall of the through-hole against which it abuts.

10. The reinforced bone plug of claim 8, wherein a radius of curvature of the at least portion of the second surface that is concave is substantially equal to a radius of curvature of the second portion of the sidewall of the through-hole.

11. The reinforced bone plug of claim 10, further comprising a suture disposed in the reinforced through-hole.

12. The implant of claim 1, wherein the second lower surface further includes a first planar portion and a second planar portion that each intersect at least a portion of the sidewall of the through-hole not abutted by the first upper surface; and
   wherein the portion with a generally concave shape is disposed between the first planar portion and the second planar portion.

13. The reinforced bone plug of claim 8, wherein the bone plug is formed of bone.

14. The reinforced bone plus of claim 8, wherein the second surface further includes a first planar portion and a second planar portion that each intersect the at least second portion of the sidewall of the through-hole; and
   wherein the concave portion of the second surface is disposed between the first planar portion and the second planar portion.

15. The implant of claim 1, wherein the proximal end portion, distal end portion, and tendon are aligned along a longitudinal axis of the implant; and
   wherein the through-hole is transverse to the longitudinal axis of the implant.

16. The implant of claim 1, wherein the reinforcing insert is movable relative to the through-hole.

17. The implant of claim 1, wherein the reinforcing insert and the proximal end portion are formed of different materials.

18. The reinforced bone plug of claim 8, wherein the insert is formed of a different material than the bone plug.

* * * * *